United States Patent [19]
Auerbach

[11] 3,946,744
[45] Mar. 30, 1976

[54] ELECTROCARDIOGRAPHY SIGNAL TRANSMISSION-RECEPTION METHOD INCLUDING METHOD OF MEASURING PACEMAKER SIGNAL FREQUENCY

[75] Inventor: Albert A. Auerbach, New York, N.Y.

[73] Assignee: Medalert Corporation, New York, N.Y.

[22] Filed: Aug. 23, 1974

[21] Appl. No.: 500,069

Related U.S. Application Data

[63] Continuation of Ser. No. 257,557, May 30, 1972, abandoned.

[52] U.S. Cl..... 128/419 PT; 128/2.06 A; 128/2.1 A
[51] Int. Cl.² .......................................... A61B 5/04
[58] Field of Search ..... 128/2.05 Q, 2.05 R, 2.05 T, 128/2.06 A, 2.06 F, 2.06 G, 2.06 R, 2.06 V, 2.1 A, 2.1 R, 419 P, 419 PT; 246/33 ME, 33 M

[56] References Cited
UNITED STATES PATENTS

| | | | |
|---|---|---|---|
| 2,674,992 | 4/1954 | Gilson et al. | 128/2.06 G |
| 2,756,404 | 7/1956 | Anderson et al. | 346/33 M |
| 3,474,353 | 10/1969 | Keller, Jr. | 128/419 PT |
| 3,599,627 | 8/1971 | Millen | 128/2.05 T |
| 3,724,455 | 4/1973 | Unger | 128/2.06 A |
| 3,742,938 | 7/1973 | Stern | 128/2.06 R |
| 3,782,367 | 1/1974 | Hochberg et al. | 128/2.06 A |
| 3,824,990 | 7/1974 | Baule | 128/2.06 G |

OTHER PUBLICATIONS
Hagan, et al., "American Journal of Medical Electronics", Apr.–June, 1963, pp. 147–151.

Primary Examiner—William E. Kamm
Attorney, Agent, or Firm—Yuter & Rosen

[57] ABSTRACT

Described is method and apparatus for transmission of electrocardiography (EKG) signal wave trains from a patient's location via common carrier wire lines, such as telephone lines, to a central diagnostic office. The EKG signals consist of a composite train of Pacemaker potentials (artifacts) derived from an implanted Pacemaker, and of potentials derived from the heart itself. At the central, the EKG signals are pen-recorded, but additionally a train of Pacemaker artifacts only, is formed and from it is determined the Pacemaker frequency as an indication of remaining Pacemaker battery life. The central is provided with additional equipment, such as an arrhythmia analyzer which prepares an interval histogram from the patient's EKG signal. The histogram serves as an indication of "loss of capture" of the patient's heartbeat by the Pacemaker and such loss of capture is confirmed by the absence of correlation between the Pacemaker artifact and the "QRS complex" portion of the patient's EKG.

Also disclosed is a method and apparatus for precisely measuring the frequency of the Pacemaker artifacts in order to detect potential Pacemaker battery failure, which would be indicated by a change in the artifact frequency over a period of time. This apparatus includes timer marker generation means for recording precisely timed markers to provide a correction factor for compensating for a variation in the recording paper speed.

13 Claims, 5 Drawing Figures

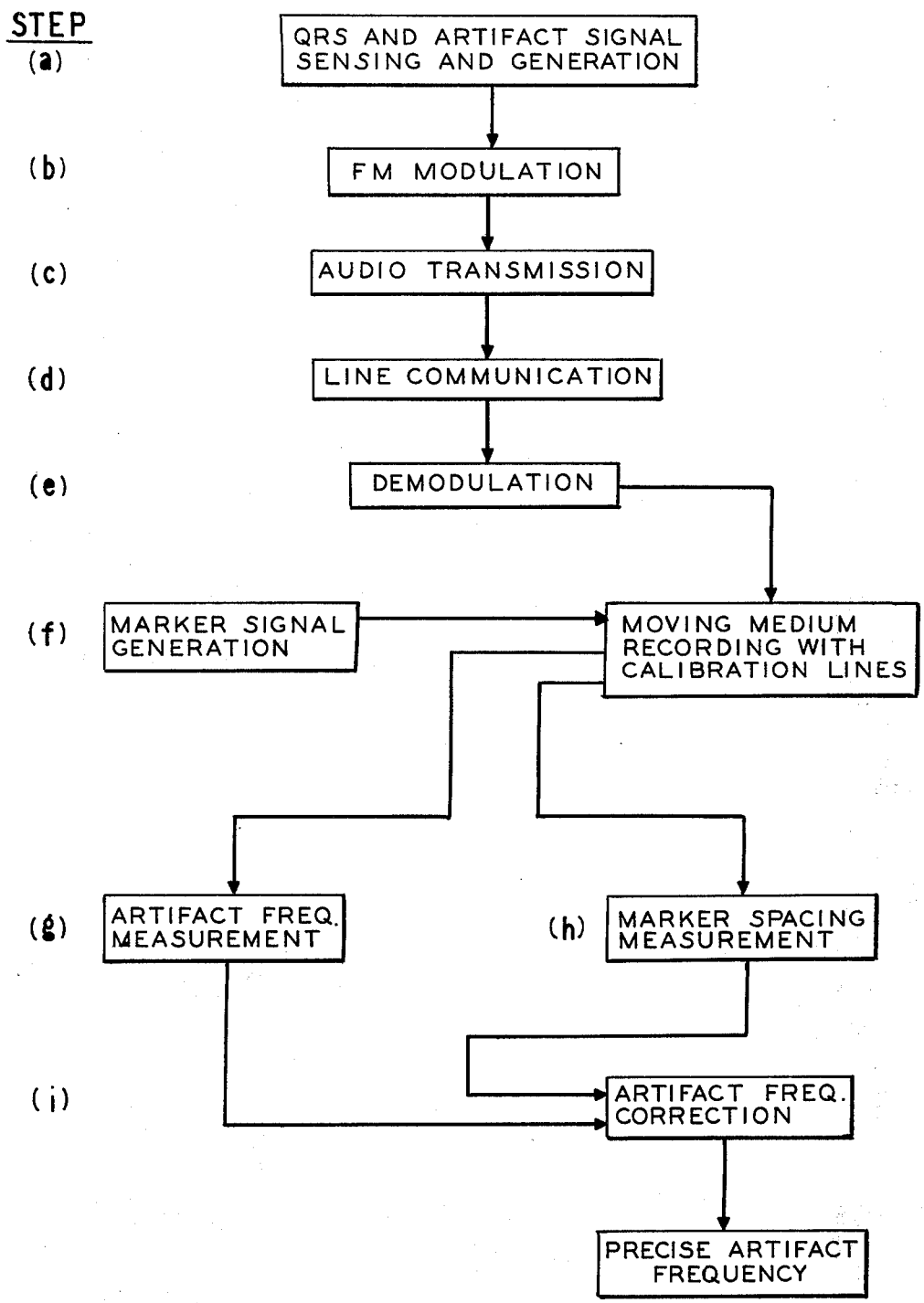

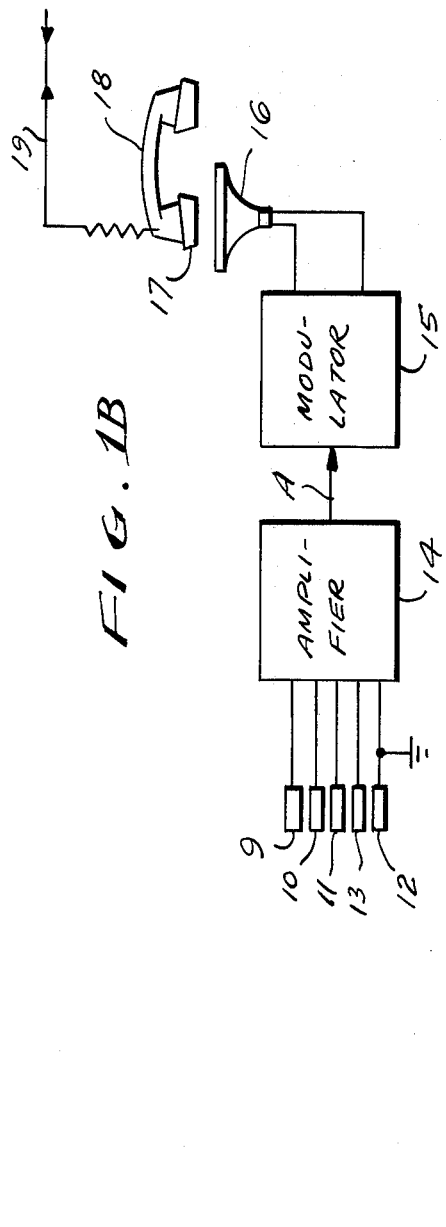
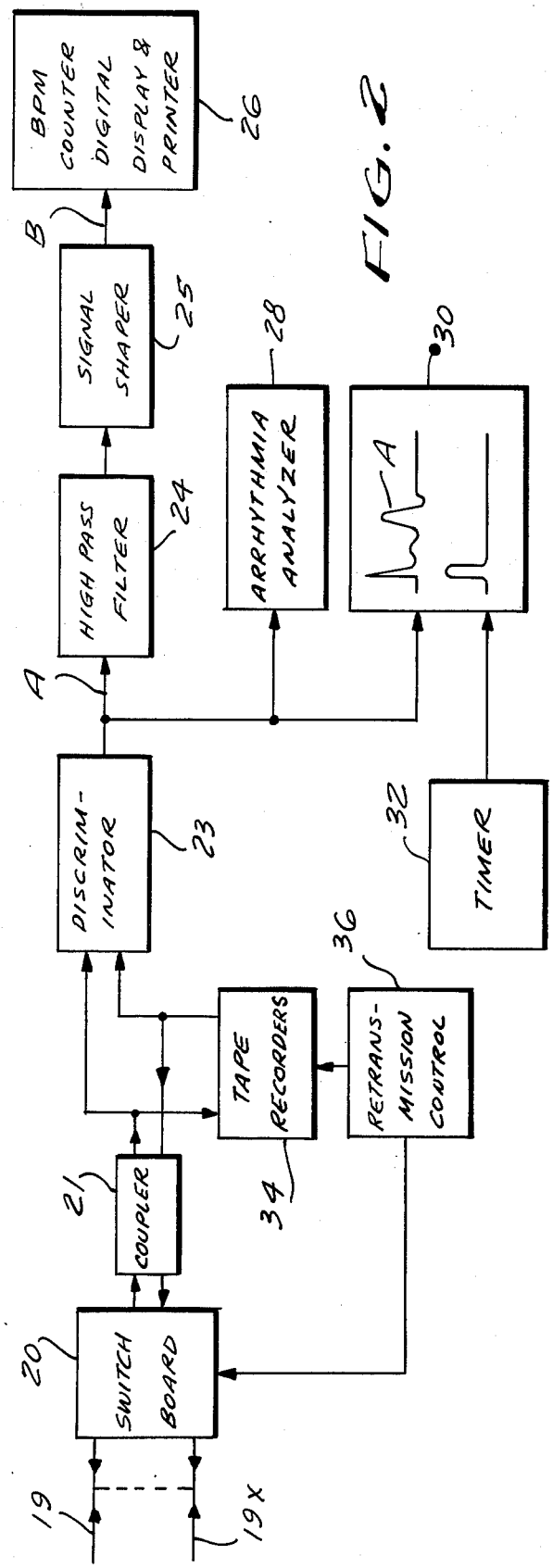

ELECTROCARDIOGRAPHY SIGNAL TRANSMISSION-RECEPTION METHOD INCLUDING METHOD OF MEASURING PACEMAKER SIGNAL FREQUENCY

This application is a continuation of application Ser. No. 257,557 filed May 30, 1972, now abandoned.

This invention relates to electrocardiography (EKG) signal transmission-reception method and apparatus, and more particularly to transmission from a patient's location via common carrier wire lines, preferably telephone lines, to a central diagnostic office. In this text, the terms "central," "central office", "central diagnostic office," are used interchangeably; the terms are not limited to a "central" in the usual telephony sense, but are applicable also to a hospital, a clinic, or even a single cardiologist's office or even a general practitioner's office, provided required equipment is present at that location.

EKG signal transmission schemes of the general character as contemplated by the present invention, have been previously proposed, but have not taken into account the peculiar problems which arise out of the use of the Pacemaker. The present invention has among its objects, the provision of EKG signal transmission-reception for patients with Pacemaker.

Beginning in the late nineteen-sixties, the Pacemaker has come into widespread use by cardiac patients. The Pacemaker is a heart-beat stimulator implanted in the patient's body. The most commonly used Pacemaker are designed to be inactive for so long as the patient's natural heart-beat rate is equal to or greater than a minimum rate acceptable for the particular patient. Whenever the patient's heart-beat rate slips below the minimum rate, the Pacemaker becomes active or "paces" to stimulate the heart beat. Above this rate Pacemaker stimuli are suppressed.

The pacing action is discernible in the electrocardiogram as a signal or "spike" of distinctive waveshape, herein also referred to as "artifact". The just described mode of Pacemaker operation is known as the "demand" mode in the sense that the Pacemaker operates only when needed or "demanded", and is otherwise inactive.

The Pacemaker is battery-powered; the life of the battery, although quite long is nevertheless finite; reduction in performance of the battery, and certainly erratic performance or total failure of the battery can be quite dangerous or even fatal to the patient. It therefore behooves to test the battery periodically to determine remaining useful battery life, and possible necessity for surgical replacement of the implanted Pacemaker including its battery.

In order to test the battery, it had been heretofore the practice to switch the Pacemaker from the demand mode to a "fixed" mode, in which the Pacemaker operates at a fixed frequency independent of the patient's heart-beat rate. Switching to the fixed mode is accomplished by placing a permanent magnet over the Pacemaker, externally to the patient's body. For the fixed mode, and in rather great contrast to the demand-mode action, the Pacemaker artifact is detectable at regular precise intervals. As a result, the Pacemaker induced heart rhythm may compete with the natural and independent rhythm of the heart. Under such conditions it is possible for the heart to stop beating normally and enter a state of fibrillation with possible fatal results.

Heretofore it had been the practice, for purposes of periodically checking battery life, to have the Pacemaker operate in the fixed mode, and measure the fixed-mode operating frequency. Change in operating frequency is an indication of future reduction in performance, or even total failure of the battery.

There exist no technological obstacles to measuring the Pacemaker fixed rate at a remotely located central, and it is within the purview of the present invention to do just that. However, there exist psychological obstacles to such measurements. The present invention contemplates that the patient transmit EKG signals to the central, even without supervision of a physician or of anyone else; that is, completely on his own. Many patients refuse to perform the things necessary to transfer to the fixed mode, namely, placing the magnet over the Pacemaker; this stems from unwillingness or fear to disturb something which appears to be functioning well and to which the patient owes his continuing life.

Not only the patients but also quite a few doctors are reluctant to operate the Pacemaker fixed mode, for fear of inducing fibrillation, as noted above; this is certainly a theoretical possibility, but has not happened even once as far as is known.

In arriving at the present invention, it was discovered that periodic measurement of the Pacemaker artifact frequency, even in the demand mode, is a good and reliable indication of residual battery life. This assumes, of course, that the Pacemaker artifacts have not been suppressed, as is generally the case. For this purpose, it is desirable to derive at the central, from the composite received EKG plus artifact signal train, a train consisting solely of artifact-corresponding signals, and measure their repetition rate. The present invention contemplates electrocardiography transmissions of the order of one minute; if during such a time interval there occurred as few as just two sequential artifacts in the demand mode, their time spacing would be a good indicator, considered in a history of similar periodic measurements, of the remaining useful battery life. In addition, measurements may be made in fixed mode Pacemaker operation since the artifacts are present on a regular basis. Timed marker signals permit precise measurement of the artifact frequency.

The present invention thus enables measuring at the diagnostic central, of the artifact frequency to the accuracy required to forecast battery failures. In addition, the described system not only checks the condition of the Pacemaker battery but also permits evaluation of possible failures in the mechanisms of interaction between the Pacemaker and the heart (such as failure to sense a conducted beat, or failure to properly stimulate the heart because of a damaged or inoperative catheter) which result in "loss of capture."

Previously proposed EKG signal transmission schemes had a major shortcoming, the overcoming of which is an object of this invention, namely, the transmitting apparatus could be provided only as "fixed station", that is at a "permanent" location and as a "permanent" installation. In contrast, by the present invention it is possible to attach the transmitting apparatus quickly at well-nigh any location equipped with a telephone, for only so long as the transmission is required, and thereafter remove it just as quickly, and without the need, at the transmitter or the telephone, of permanent and expensive coupling devices. In this manner, the transmission may be effected by the doctor, or even by the patient himself, from the patient's home, or wherever the patient may be located, either under emergency conditions, or as part of a periodic electrocardiography program.

Other objects, features and advantages of the invention will be apparent from the following more detailed description, of which the appended claims form a part, considered together with the accompanying drawings, in which:

FIG. 1A is a block diagram of the preferred method of precisely measuring Pacemaker artifact frequency.

FIG. 1B is a block diagram of the equipment at the patient's or transmitting location;

FIG. 2 is a block diagram of the diagnostic central, or receiving location, both in accordance with a preferred embodiment of the invention;

The following description is presented as applied to a patient with implanted Pacemaker. Of the several signals or waveshapes obtainable by EKG methods, which waveshapes are known as "complexes", "segments" and "waves," the single one which by itself is most prominent is the QRS complex illustrated in waveform A of FIG. 3. The QRS complex results from depolarization of the ventricles prior to contraction. It is substantially coincident with the actual contraction of the cardiac muscle, which produces the pumping action. The QRS complex has in the case of a healthy heart, a relatively rapid rise and fall; the interval between half amplitude points may be typically about 0.04 seconds, and this width may increase when the heart muscle is damaged.

Figure 3:
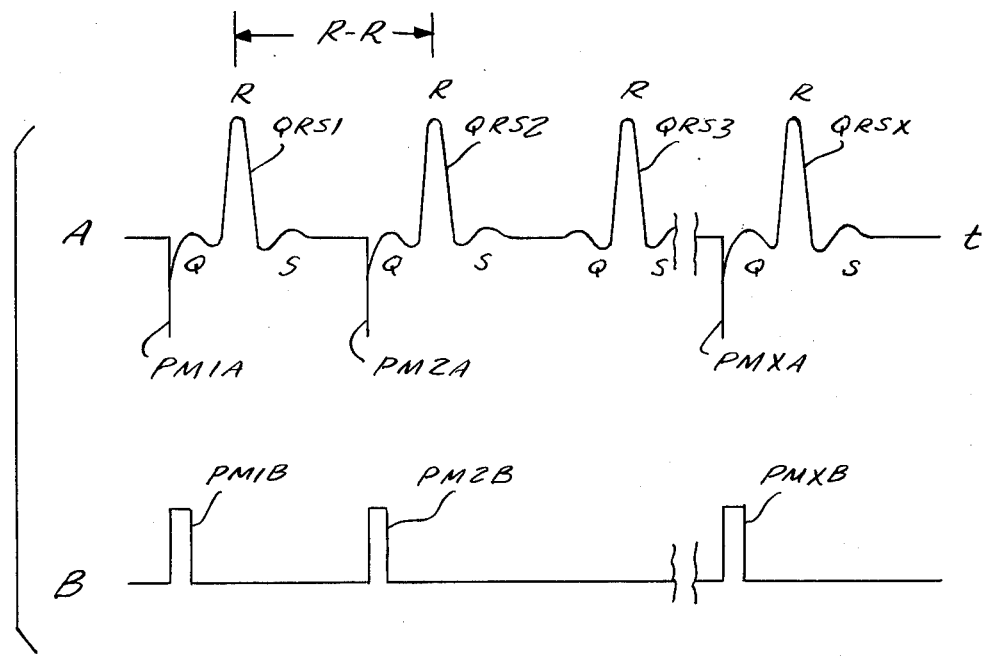
FIG. 3 is a waveshape diagram useful in the interpretation of FIGS. 1B and 2.

For purposes of FIG. 3, it is assumed that the patient is equipped with a Pacemaker operating in the demand mode. Illustrated are a number of QRS complexes QRS1, QRS2 ... QRSx (observe the "break" in the time-axis following QRS3), but only some, and more specifically, complexes QRS1, QRS2 and QRSx, are preceded by Pacemaker "spikes" or artifacts, PM1A, PM2A and PMXA, respectively. In the fixed mode, each QRS complex would be preceded by a Pacemaker artifact. And in the use of a patient without Pacemaker, no artifacts would appear at all.

For a patient equipped with a Pacemaker, the QRS complex will be preceded by a Pacemaker "spike" or "artifact", designated in FIG. 3 as PM. Whereas the upper limit of the significant spectral components of the QRS complex is of the order of 80 Hz, those of the Pacemaker artifacts are somewhat higher, approaching 200 Hz; advantage of this fact is taken in separating out Pacemaker spikes, as described below with reference to FIG. 2.

In the composite Pacemaker artifact-QRS complex wave train A, an artifact PM precedes the QRS signal by a variable amount, here arbitrarily taken as about 0.06 seconds; the period for complete repetition of a composite PM-QRS signal for the fixed mode is arbitrarily taken as 0.8 seconds.

Referring to FIG. 1B, before transmission to the diagnostic central of FIG. 2 begins, the patient will have attached to standard points on his body, EKG electrodes designated in FIG. 1 as 9 to 13. For satisfactory detection of the EKG and PM signals, a minimum of two electrodes is required; these are usually the right and left arm electrodes 9 and 10. When additional information is required three additional electrodes 11, 12, 13 are utilized; these are, in order, a left leg electrode; a right leg electrode (also known as indifferent or ground electrode); and a chest electrode (also known as precordial electrode). These will have been connected, for example by plug-in connector (not shown) into an amplifier 14, which accordingly delivers at its output an amplified version of the waveshape A. The amplifier may be of the type conventional for EKG purposes, but owing to the higher frequency components of the Pacemaker artifact PM, will have a higher upper cut-off frequency. In a working embodiment, the amplifier 14 was given lower and upper down-three-decibel frequencies of 0.25 and 80 Hz respectively. Higher frequency Pacemaker components are also transmitted since their amplitude is considerably greater than the EKG signals. To suppress the conventional power line frequency, 60 Hz in the United States, the amplifier 14 is designed for "balanced" dual input with consequent common-mode suppression, that is self-cancellation of in-phase power-line and other pickup noise signals at the electrodes 9 and 10. For this purpose, advantageously the right leg electrode 12 is placed on the patient's body and is grounded as shown. The amplifier 14 is battery-powered in order to maximize portability of the unit.

The amplified output signal A is applied to a frequency modulator or voltage-controlled oscillator 15, which operates at a carrier frequency in the middle audio frequency range, typically 1800 Hz, with maximum frequency deviation of about ± 25% or ± 450 Hz. The instant frequency deviation from carrier frequency is proportional to the instant amplitude of the signal in wavetrain A, thus giving rise to the term "voltage-controlled oscillator." For purposes of this text frequency modulation and phase modulation shall be considered synonymous.

The output of the modulator 15 drives a loudspeaker 16 which accordingly produces sound output in a frequency range from 1350 Hz to 2250 Hz.

The description so far given is preparatory to transmission of the EKG signals. Transmission is initiated by telephone dialing the diagnostic central, utilizing the telephone set 18 at the patient's station, via outgoing telephone lines indicated symbolically as 19; the double ended arrow signifies facility for two-way communication. When voice communication with the central has been established, and when readiness at both ends has been acknowledged, the telephone set 18 is placed with the mouthpiece 17 in proximity to or even placed directly over, the loudspeaker 16. Such direct acoustic coupling is in line with the objective of utilizing the equipment well-nigh anywhere. Transmission of the modulated carrier is thus commenced, and continued usually for a preagreed time of the order of 1 minute; this to afford the possibility of further voice communication.

A suitable EKG transmitter is disclosed in U.S. Pat. No. 3,872,251 filed Feb. 20, 1973 for Electrocardiography Transmitter and Transmission Method and issued Mar. 18, 1975 to the same assignee.

Referring to FIG. 2, the line 19 is shown symbolically as connected to a switchboard 20 at the central, along with numerous other lines the last of which is designated as 19x. The showing of plural lines may be considered symbolic, since in principle the invention may be practiced with the single telephone subscriber's line assigned to the central. However the plural lines 19, etc. may include plural public lines, to accommodate plural incoming calls simultaneously, and may even include private lines to cardiologist's offices. The switchboard 20 may be Model 507 manufactured by Western Electric Co., and as such affords facility for receiving incoming calls, dialing outgoing calls, voice communication, connections to various extensions, facility for multi-party conference connections, etc.

The receiving station equipment proper may be considered to be the units shown to the right of the switchboard 20. When voice acknowledgement has been made between patient's station with the attendant at the switchboard 20, as adverted to in the description of FIG. 1B, the attendant interconnects at the switchboard 20, the incoming call-line 19, now transmitting the modulated carrier, with the receiving equipment, and more particularly with a coupler or set of couplers 21, which may be of the RDY type, manufactured by the Western Electric Company. The couplers 21 are provided primarily for the purpose of isolating the telephone lines, in both directions, but they are not absolutely essential.

From the coupler 21, the received modulated carrier is inserted into a well-known frequency discriminator 23, which reproduces the original wavetrain A at its output. The thus reproduced or recovered wavetrain A is applied to inputs of a high-pass filter 24 (which in turn feeds a signal shaper 25, which is followed by a beats-per-minute counter digital display and printer 26), an arrhythmia analyzer 28, and to an EKG pen-recording mechanism 30 which accordingly plots the electrocardiograph on standard EKG paper; note the reproduced trace A within unit 30.

The pen-recording mechanism 30 may be considered a minimum requirement for a diagnostic central; the EKG trace is of itself sufficient to provide a basis for determining all the other data provided by the units 26 and 28, however with lesser accuracy, for the following reasons.

In accordance with standard practice the paper moves at a speed of 25 millimeters per second, and is accurately ruled every millimeter. A frequency measurement is usually made by the human interpreter over a 12 second interval. The number of Pacemaker spike-to-spike intervals (including fractional intervals) is measured within a convenient 30 centimeter space, and the result, multiplied by five, is the Pacemaker spike frequency in beats per minute. This result, however, may be inaccurate by several percent because the paper speed varies with several uncontrolled factors, such as power line frequency, variable paper drag, etc.

In accordance with the invention, correction for the inaccuracy is made by having a timer 32 actuate a second pen-recorder typically every 3 seconds. This produces a second, parallel trace (see unit 30) of time markers. The number of millimeters separating 11 consecutive markers made by this pen should be 750, if the speed is precisely 2.5 cm per second. The actual number of millimeters separating 11 such markers is counted. If this actual number is "$x$", the factor ($x/750$) is a required correction on the frequency measured above, i.e., the true Pacemaker spike frequency will be the measured frequency multiplied by the factor "$x/750$". Since the time markers can be measured to better than 0.2 millimeters, the paper speed is thus calibrated to better than 1 part in 3750, which allows the Pacemaker spike frequency to be measured to better than 0.1 beats per minute (in contrast, the accuracy of the unit 26 is about 1 part in 5000). Timer 32 may be a crystal oscillator with an output frequency of 3 pulses per second, of the type manufactured by Fork Standard Corporation, West Chicago, Illinois. The accuracy of unit 30 is desirable for Pacemaker patients and is considerably higher than is customarily accepted in electrocardiography as applied to a patient without Pacemaker. Thus the just described feature of the invention may of itself be sufficient to provide, at lesser accuracy to be sure, an approximation of the data available from the units 26 and 28, or may serve as a redundancy device to safeguard against failures or malfunctions of these units. In concluding part of the description there are given further examples of interpretation of the data produced by units 26, 28 and 30.

FIG. 1A is a flow chart of the overall method of precisely measuring the Pacemaker artifact frequency when EKG data is transmitted from a first location to a receiving location. The EKG data includes information relating to the heartbeat of a patient and the Pacemaker implanted in the patient's body. The purpose of the method is to precisely measure the frequency of the artifact signals to accurately assess the residual life of the battery or other power source of the Pacemaker, or any artificial heart stimulator. The method comprises the following steps:

a. sensing and generating a train of repetitive composite signals which include a plurality of QRS complex signals attributable to the heartbeat of the patient and a plurality of artifact signals attributable to the operation of the heart stimulator and wherein the artifact signals are interspersed with the QRS complex signals;

b. frequency-modulating the train of signals onto a carrier signal having a carrier frequency in the audio frequency range;

c. transmitting the frequency-modulated carrier to the receiving location via ordinary communication carrier lines;

d. demodulating, at the receiving location, the incoming frequency-modulated carrier signal to reproduce a signal train which has a waveform corresponding to the original signal train;

e. recording the reproduced signal train on a moving recording medium having equally-spaced calibration lines and designed to move at a desired speed;

f. generating and recording on the recording medium, at substantially the same time as the recording of the reproduced signal train, and completely independent from the recording medium moving means, periodically-timed marker signals spaced in time so that during that time the moving recording medium will move a desired space relative to the marker signals when at the desired speed;

g. measuring the linear distance between sequential artifact signals on the recording medium as indicated by the calibration lines to determine the measured artifact signal frequency, assuming that the recording medium is moving at the desired speed;

h. measuring the space between selected marker signals to determine if the moving recording medium was moving at the desired speed during the recording, thereby indicating that the measured artifact signal frequency is the correct artifact signal frequency;

i. and obtaining the precise artifact signal frequency if the moving recording medium was not-moving at the desired speed by correcting the measured artifact signal frequency in accordance with a correction factor determined by the ratio between the measured space between the selected marker signals and the desired space when the moving recording medium is moving at the desired speed.

The high-pass filter 24 serves to filter out those lower-frequency components in wavetrain A, which are due to the QRS complex and other components of the EKG, and thus serves to provide via signal shaper 25 a signal train B (see FIG. 3) consisting of reshaped pulses derived from the Pacemaker artifacts PM. The signal train B is applied to a counter 26, which is preferably of the type manufactured by Monsanto Company, Type 107A, which has the capability of measuring and digitally displaying time intervals between successive input signals (here, the pulses in waveshape B) and also their frequency expressed in beats per minute, to an accuracy of 1 part in 5000 as previously stated.

The repetition rate of the Pacemaker artifacts (see FIG. 3) remains fairly constant throughout the life of the Pacemaker battery, but tends to change by several percent near the end of the battery life, and this is true not only for fixed mode operation, but also for demand mode operation; for the demand mode the resolution accuracy of frequency measurement is necessarily reduced, but is still sufficient for forewarning potential failure of the Pacemaker battery life.

Figure 4:
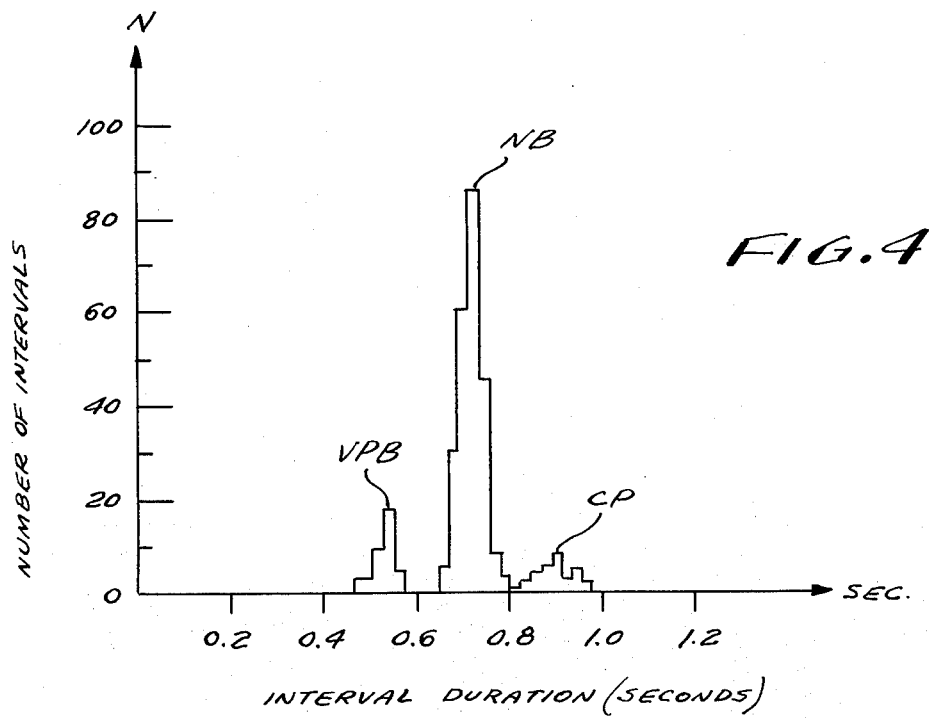
FIG. 4 is a "histogram", that is, a graphical statistical synopsis machine-prepared in response to the EKG signals received at the central illustrated in FIG. 2.

The arrhythmia analyzer 28 may be of the kind manufactured by Instruments for Cardiac Research. When the "demand mode" EKG is transmitted and recorded, the unit 28 measures R—R intervals between consecutive R-waves (see FIG. 3) and groups these intervals into 20 millisecond classes. The number of intervals in each class is counted, and the counts are displayed as a function of the interval duration as shown in FIG. 4, by the arrhythmia analyzer 28. From the displayed data, it is possible to compute an average R—R interval from the succession of QRS complexes, and to compute the coefficient of variation (CV) of the R—R intervals. The various graphs or clusters shown in FIG. 4 are an indication of the statistical distribution of R—R intervals of various durations. The significance of these clusters will be explained in the concluding part of the description. The description so far given has been for "real time" operation of the diagnostic central of FIG. 2; however, it is desirable for some purposes, to have available the facility of having the functions of the units 26, 28, 30 or of units equivalent to them, at a later time. Such purposes are, amongst others:

As a redundancy safeguard against possible malfunction or failure of the equipment.

For re-constructing the final output records at a future time.

For generating the final output records in the first instance, later, when the equipment is busy with an earlier-commenced transmission.

For re-transmitting the transmission (voice and EKG, if desired) to another "central", for example a cardiologist's office.

Accordingly, the coupler 21 is also connected, and bidirectionally so, to a magnetic tape recorder 34, which under control of a retransmission control unit 36, may be switched in and out to record the incoming transmission, for concurrent real time processing by the units 26, 28, 30, or upon playback for subsequent processing; or for retransmission via switchboard and an outgoing line, again on a concurrent or a subsequent basis.

The described method and system is highly versatile and advantageous; amongst the many possible uses and advantages are the following:

The described system checks both the condition of the Pacemaker battery and "loss of capture" of the heart beat by the Pacemaker.

Lack of capture (adverted to in the specification introduction), either due to failure to sense the conducted beat or failure to stimulate the left ventricle, may be determined both by direct observation of the total EKG as well as by measurement of the coefficient of variation (CV) of the R—R interval. Direct observation of the total EKG indicates that the Pacemaker spike and the QRS complex no longer maintain an essentially constant phase relationship when there is "loss of capture." On other occasions, the QRS complex is missing altogether, despite the presence of the Pacemaker spike. The variability of the QRS complex (or its absence) is apparent to the trained cardiologist by direct observation of the total EKG record.

The normal variability of the QRS complex gives rise to a coefficient of variation (CV) usually on the order of 3–5%. During loss of capture, the variability exceeds 10%. This is recognized on the interval histogram (see FIG. 4) as a cluster of premature beats VPB, a normal cluster NB somewhat displaced in time (with a longer period), and a third cluster CP of "compensatory pauses," with an abnormally long period. The numerical value of the CV of such an interval histogram is consequently greater than normal. An increase in this CV quantifies the visual observation made by the cardiologist and thus helps define the specific Pacemaker defect. Under normal conditions, solely the cluster NB would be present. With the Pacemaker even in its normal demand mode, the EKG record itself, and the R—R interval histogram, indicate whether the heart Pacemaker interaction is normal. The data thus extracted from the transmitted signal is plotted for each transmission (usually monthly, but more often than once per month at the beginning and end of Pacemaker battery life). Changes in these extracted parameters (Pacemaker spike frequency and coefficient of variation), together with a cardiological interpretation of the transmitted EKG, permit a determination of the need for surgical replacement of the Pacemaker or of its catheter sensing and stimulating electrode.

What is claimed is:

1. A method of transmitting electrocardiographic data from a first location to a receiving location, wherein the data includes information relating to the heartbeat of a patient and an artificial heart stimulator implanted in the patient's body for precisely measuring the frequency of the artifact signals to accurately assess the residual life of the power source of the artificial heart stimulator, said method comprising:

a. sensing and generating a train of repetitive composite signals which include a plurality of QRS complex signals attributable to the heartbeat of the patient and a plurality of artifact signals attributable to the operation of the heart stimulator and wherein the artifact signals are interspersed with the QRS complex signals;

b. frequency-modulating the train of signals onto a carrier signal having a carrier frequency in the audio frequency range;

c. transmitting the frequency-modulated carrier to the receiving location via ordinary communication carriers lines;

d. demodulating, at the receiving location, the incoming frequency-modulated carrier signal to reproduce a signal train which has a waveform corresponding to the original signal train;

e. recording the reproduced signal train on a moving recording medium having equally-spaced calibration lines and designed to move at a desired speed;

f. generating and recording on the recording medium, at substantially the same time as the recording of the reproduced signal train, and completely independent from the recording medium moving means, periodically-timed marker signals spaced in time so that during that time the moving recording medium will move a desired space relative to the marker signals when at the desired speed;

g. measuring the linear distance between sequential artifact signals on the recording medium as indicated by the calibration lines to determine the measured artifact signal frequency, assuming that the recording medium is moving at the desired speed;

h. measuring the space between selected marker signals to determine if the moving recording medium was moving at the desired speed during the recording, thereby indicating that the measured artifact signal frequency is the correct artifact signal frequency;

i. and obtaining the precise artifact signal frequency if the moving recording medium was not moving at the desired speed by correcting the measured artifact signal frequency in accordance with a correction factor determined by the ratio between the measured space between the selected marker signals and the desired space when the moving recording medium is moving at the desired speed.

2. A method as claimed in claim 1, further comprising the step of deriving and displaying, at the receiving location, from the reproduced signal train, a separate signal train which contains solely signals which correspond time-wise to the original artifact signals.

3. A method as claimed in claim 2 further comprising measuring at the receiving location by means of an interval counter the artifact-to-artifact time intervals in the derived artifact signal train.

4. A method as claimed in claim 3 comprising machine-computing from the measured artifact-to-artifact time intervals, the artifact frequency.

5. A method as claimed in claim 4 further comprising applying the reproduced signal train to an arrhythmia analyzer for computation, and automatic display by the arrhythmia analyzer, of a "histogram" of the received electrocardiographic information.

6. A method as claimed in claim 1 further comprising retransmitting from the receiving location to a remote location, a frequency-modulated signal equivalent to the frequency-modulated signal received from the patient's location, demodulating, at the remote location, the incoming frequency-modulated carrier signal to recover a signal train which corresponds to the original signal train, and displaying the recovered signal train at the remote location.

7. A method as claimed in claim 1 wherein the communication lines are telephone lines to which are linked telephone transmitting-receiving equipment at the patient's location and at the receiving location.

8. A method as claimed in claim 7 further comprising recording, at the receiving location, the there received frequency-modulated signal, and at a later time, reproducing the recorded signal, transmitting the reproduced signal to a remote location via telephone lines and receiving and displaying the reproduced signal at the remote location.

9. A method as claimed in claim 7 further comprising, after the frequency-modulating step, transducing the modulated carrier into an audible signal, and acoustically coupling the latter audible signal into the patient's telephone set for transmission to the receiving location.

10. A method of precisely measuring the frequency of Pacemaker artifact signals included in electrocardiography signals recorded on a recording medium having equally-spaced calibration lines and designed to move at a desired speed comprising the steps of:

a. generating and recording on the recording medium, at substantially the same time as the recording of the electrocardiography signals and completely independent from the recording medium moving means, periodically-timed marker signals spaced in time so that during that time the moving recording medium will move a desired space relative to the marker signals when at the desired speed;

b. measuring the linear distance between sequential artifact signals on the recording medium as indicated by the calibration lines to determine the measured artifact signal frequency, assuming that the recording medium is moving at the desired speed;

c. measuring the space between selected marker signals to determine if the moving recording medium was moving at the desired speed during the recording, thereby indicating that the measured artifact signal frequency is the correct artifact signal frequency;

d. and obtaining the precise artifact signal frequency if the moving recording medium was not moving at the desired speed by correcting the measured artifact signal frequency in accordance with a correction factor determined by the ratio between the measured space between the selected marker signals and the desired space when the moving recording medium is moving at the desired speed.

11. The method of claim 10 wherein the calibration lines on the recording medium are spaced X millimeter(s) apart, the desired speed of the moving recording medium is Y millimeter(s) per second, the time spacing of the timed marker signals is one every Z second(s) and the correction factor is the number of millimeters separating U recorded markers divided by X times Y times Z times U-1, the precise artifact signal frequency being the measured artifact signal frequency multiplied by the correction factor.

12. The method of claim 24 wherein X equals 1, Y equals 25, Z equals 3 and U-1 equals 10 so that X times Y times Z times U-1 equals 750, the denominator of the correction factor.

13. The method of claim 12 further comprising the step of recording the electrocardiography signals including sequential artifacts on the moving recording medium in a first trace and the marker signals in a second trace parallel to the first trace.

* * * * *